United States Patent [19]
Chan et al.

[11] Patent Number: 5,994,596
[45] Date of Patent: Nov. 30, 1999

[54] METHOD FOR PREPARING HIGH PURITY INDANE BISPHENOLS

[75] Inventors: Kwok Pong Chan, Troy; Pamela L. Cristo, Castleton; Patrick M. McGrath, Jr., Schenectady, all of N.Y.

[73] Assignee: Molecular OptoElectronics Corporation, Watervliet, N.Y.

[21] Appl. No.: 09/052,546

[22] Filed: Mar. 31, 1998

[51] Int. Cl.$^6$ .................................................. C07C 39/12
[52] U.S. Cl. .............................................................. 568/719
[58] Field of Search ............................................. 568/719

[56] References Cited

U.S. PATENT DOCUMENTS

| | | | |
|---|---|---|---|
| 2,754,285 | 7/1956 | Petropoulos | 260/47 |
| 2,819,249 | 1/1958 | Petropoulos et al. | 260/45.95 |
| 3,288,864 | 11/1966 | Farnham | 260/619 |
| 4,334,106 | 6/1982 | Dai | 568/719 |
| 4,701,566 | 10/1987 | Faler et al. | 568/719 |
| 4,791,234 | 12/1988 | Faler et al. | 568/719 |

FOREIGN PATENT DOCUMENTS 5-294879  11/1993  Japan .

*Primary Examiner*—Michael L. Shippen
*Attorney, Agent, or Firm*—Heslin & Rothenberg, P.C.; Martha L. Boden, Esq.

[57] ABSTRACT

A process for preparing high purity indane bisphenols in high yield is disclosed. The method comprises heating a bisphenol in the presence of Montmorillonite K10 clay, which catalyzes the synthesis reaction more rapidly and effectively than other clays previously disclosed. The high purity ($\geq 97\%$) of the synthesized indane bisphenol is obtained by two successive selective recrystallizations, the first from an organic solvent, and the second from an acetic acid solution. The high purity indane bisphenols produced may be made substantially pure (>99%) by employing a purification process which includes at least one selective recrystallization from a 45%–80% by volume aqueous acetic acid solution. Alternatively, substantially pure indane bisphenol may be obtained by recrystallization from a solution of 89–93% by volume toluene and 7–11% by volume n-propanol, or by a combination of recrystallizations from toluene/n-propanol and from aqueous acetic acid. Substantially pure indane bisphenols, such as 5-hydroxy-3-(4-hydroxyphenyl)-1,1,3-trimethylindane, are suitable for conversion to high molecular weight polymers.

19 Claims, No Drawings

METHOD FOR PREPARING HIGH PURITY INDANE BISPHENOLS

The following invention was made with Government support under contract number F33615-95-C-5432 awarded by the United States Air Force. The Government has certain rights in this invention.

FIELD OF THE INVENTION

The present invention relates to the preparation of high purity indane bisphenols, and more particularly to the preparation of high purity and substantially pure indane bisphenols in high yield.

BACKGROUND OF THE INVENTION

Indane bisphenols of formula (I) below and methods for their preparation have been known for some time. Such compounds are useful in the synthesis of many polymers. For example, high molecular weight homo- and copolycarbonates comprising substituted and unsubstituted indane bisphenol monomers are disclosed and claimed in commonly owned U.S. Pat. No. 5,703,197 and copending and commonly owned application Ser. No. 08/947,980 filed Oct. 9, 1997. Such indane polycarbonates are shown to possess unique and advantageous properties. In addition, U.S. Pat. No. 3,634,089 to Hamb discloses the preparation of high molecular weight indane polyesters. Patel et al. describe poly(arylindane)ethers in U.S. Pat. No. 5,145,926, and Paul et al. disclose in U.S. Pat. No. 4,988.785 bismaleimide resins based on indane bisphenols.

Indane bisphenols, as described herein, are represented by the structural formula

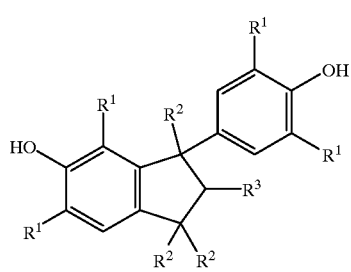

(I)

wherein each $R^1$ is independently hydrogen, deuterium, halogen, alkyl having 1 to 4 carbons, alkoxy having 1 to 4 carbons, or a deuterated equivalent thereof; each $R^2$ is an alkyl group having 1 to 4 carbons or a deuterated equivalent thereof; $R^3$ is hydrogen or deuterium when $R^2$ is methyl or its deuterated equivalent; otherwise $R^3$ is an alkyl group or a deuterated equivalent thereof having one less carbon than that of $R^2$. As used herein, "alkyl" refers to linear or branched saturated hydrocarbon residues containing 1 to 4 carbons. "Alkoxy" refers to the same residues containing, in addition, an oxygen atom at the point of attachment. "Deuterated equivalents thereof", as used herein, refers to the hydrocarbon moieties listed above for $R^1$, $R^2$, and $R^3$ in which at least one hydrogen is replaced with the deuterium isotope. For example, a deuterated methyl group may be $CDH_2$, $CD_2H$, or $CD_3$, and a deuterated ethyl may be $CH_3CD_2$.

The preparation of indane bisphenols of formula (I), also known as hydroxyphenyl indanols, is disclosed in U.S. Pat. No. 2,754,285 to Petropoulos and U.S. Pat. No. 2,819,249 to Petropoulos et al. via an acid-catalyzed dimerization of a-methyl styrene to form indanes, followed by sulfonation of the indanes, and heating the sulfonated product with potassium hydroxide to yield 5-hydroxy-3-(4-hydroxyphenyl)-1,1,3-trimethylindane, wherein each $R^1$ and $R^3$ is hydrogen, and $R^2$ is methyl in structure (I) above. 5-Hydroxy-3-(4-hydroxyphenyl)-1,1,3-trimethylindane is also referred to herein as "IBP".

U.S. Pat. No. 3,288,864 to Farnham discloses a method of IBP production which comprises treating isopropenylphenol (IPP) with a Friedel-Crafts catalyst at elevated temperatures. U.S. Pat. No. 4,334,106 to Dai discloses somewhat milder reaction conditions in treating IPP or a mixture of its linear oligomers with a stoichiometric excess of organic acid. U.S. Pat. No. 4,791,234 to Faler et al. describes that a decrease in the amount of organic acid used to catalyze the rearrangement of bisphenol A (also referred to herein as "BPA") to form 6,6'-dihydroxy-3,3,3',3'-tetramethyl-1,1'-spirobiindane (hereinafter, "SBI") leads to the formation of IBP in concentrations of up to 50% in the reaction mixture.

The reaction conditions were further simplified in Japanese Application No. 05294879 which describes a method of producing IBP by treating BPA with an activated clay prepared by Nippon Kassei Hakudo Co. (K-500) at temperatures between 100°–180° C. However, this method requires a lengthy 3–5 hour reaction time. At the completion of the reaction, IBP is precipitated from toluene yielding crystals having a purity between 57% and 78%. Further purification is possible via recrystallization from an aromatic solvent such as toluene, to obtain IBP having a maximum purity of 96% in a 28% yield.

The present invention provides a method for increasing indane bisphenol purity and yield. High purity indane bisphenols (at least 97% pure) previously unreported and in higher yields (34% theoretical) may now be prepared using the present method. In addition, under certain experimental conditions, the present invention allows the reaction time to be significantly cut to as low as 15 minutes. Using a novel set of mild isolation and purification procedures disclosed herein, substantially pure indane bisphenols having a purity of >99% may also be prepared with the present method. These substantially pure materials can then be converted to high molecular weight indane polymers as set forth in the references above.

SUMMARY OF THE INVENTION

The present invention is based on the unexpected discovery that Montmorillonite K10 clay catalyzes the indane bisphenol synthesis reaction more rapidly and more effectively than other clays previously claimed or tested, leading to the rapid formation of a high purity product in high yield. In addition, the process described herein for isolation and subsequent purification by selective recrystallizations from aqueous acetic acid and/or from a solution of n-propanol and toluene provides indane bisphenols with surprisingly excellent purity (typically >99%) in high yield. These substantially pure indane bisphenols are useful for the preparation of homo- and copolymers of very high molecular weight.

In one of its aspects, the invention includes a method for preparing a high purity ($\geq 97\%$) indane bisphenol of formula (I), which comprises the step of
(a) heating a mixture comprising
(i) a bisphenol having the formula

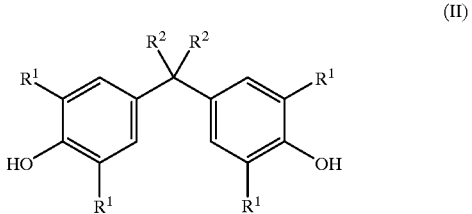

(II)

wherein $R^1$ and $R^2$ are as previously defined; and
(ii) a clay catalyst comprising Montmorillonite K10 at a temperature in the range of about 100°–180° C. for a time sufficient to produce a crude indane bisphenol, by-products, and impurities in admixture with the clay catalyst. The reaction is depicted as follows:

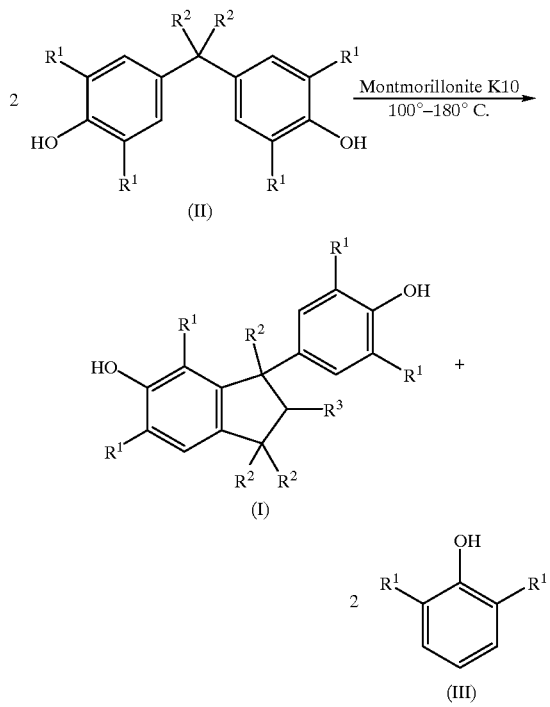

The method also includes the following steps after step (a) above:
(b) adding an organic solvent to the crude indane bisphenol, by-products, impurities, and the clay catalyst, wherein the organic solvent is toluene, ethylbenzene, cumene, benzene, chlorobenzene, trichloroethane, or tetrachloroethane;
(c) dissolving in the organic solvent the crude indane bisphenol, by-products, and impurities to form a product solution in admixture with the clay catalyst;
(d) removing the clay catalyst from the product solution;
(e) allowing crude crystals containing the crude indane bisphenol to precipitate from the product solution;
(f) recovering the crude crystals; and
(g) further purifying the crude crystals by dissolution in acetic acid followed by a second precipitation.

In another aspect, the invention includes a method for preparing a high purity indane bisphenol of formula (I) using the procedure outlined above with the exception that the organic solvent is added as one of the reagents in heating step (a). Thus, the product solution also includes the organic solvent.

In another aspect, the method allows the recovery of additional crude indane bisphenol crystals prior to the purifying step (g) above by removing from the crude crystals which precipitated in step (e) the product solution remaining after the precipitation. The remaining product solution contains a major proportion of the by-products and impurities including phenols of the formula (III) given above, spirobiindane bisphenols of the formula (IV) given below, and unreacted bisphenol of formula (II), wherein $R^1$, $R^2$, and $R^3$ are as previously defined. The organic solvent and phenols (III) may then be removed from the remaining product solution to leave a material comprising an additional crude indane bisphenol, spirobiindane bisphenol of formula (IV), and unreacted bisphenol of formula (II). This material is then dissolved in an organic liquid followed by an additional precipitation of crude indane bisphenol crystals. The crude crystals are then removed from the organic liquid and may be further purified, as described above, to increase the yield of the high purity indane bisphenol (I).

In yet another aspect, the invention is a method for further purifying the high purity indane bisphenol to produce a high purity indane bisphenol in substantially pure form. The further purification is effected by at least one selective recrystallization from a 45%–80% by volume aqueous acetic acid solution, or by a selective recrystallization from a solution of 89–93% by volume toluene and 7–11% by volume n-propanol, or by a combination of recrystallizations from a solution of 89–93% by volume toluene/7–11% by volume n-propanol and from a 45%–80% by volume aqueous acetic acid solution.

In yet another aspect, the invention is substantially pure 5-hydroxy-3-(4-hydroxyphenyl)-1,1,3-trimethylindane having an absorbance at 350 nanometers of at most 0.003 as measured on a solution of 1 gram thereof in 100 mL spectroscopic grade methanol.

In yet another aspect, the invention is substantially pure 5-hydroxy-3-(4-hydroxyphenyl)-1,1,3-trimethylindane having an absorbance at 350 nanometers of at most 0.001 as measured on a solution of 1 gram thereof in 100 mL spectroscopic grade methanol.

DESCRIPTION OF THE PREFERRED EMBODIMENTS

The indane bisphenols of formula (I) which may be produced by the present method include IBP, which is usually preferred. Also included are various substituted analogs of IBP, wherein $R^1$, $R^2$, and $R^3$ are defined above. Illustrative useful $R^1$ substituents are hydrogen, bromo-, chloro-, various alkyl groups such as methyl, ethyl, propyl, isopropyl, butyl, sec-butyl, and the like, and alkoxy groups such as methoxy, ethoxy, propoxy, and butoxy. In addition, deuterated substituents in which at least one hydrogen is replaced with the deuterium isotope may be employed.

As stated above, a particularly preferred indane bisphenol (I) is IBP, or 5-hydroxy-3-(4-hydroxyphenyl)-1,1,3-trimethylindane, wherein each $R^1$ and $R^3$ is hydrogen, and each $R^2$ is a methyl group, as shown by the following structural formula

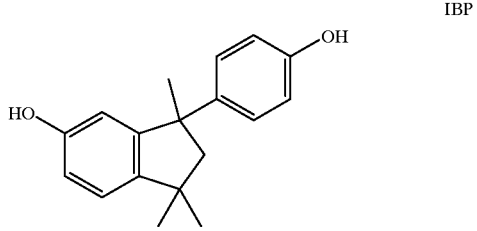

IBP

Bisphenol compounds of structure (II) for use as reactants in the practice of this invention can be obtained from commercial sources. Illustrative bisphenols include 2,2-bis(4-hydroxyphenyl)propane, commonly known as bisphenol A or BPA, 3,3-bis(4-hydroxyphenyl)pentane, 4,4-bis(4-hydroxyphenyl)heptane, 2,2-bis(3,5-dibromo-4-hydroxyphenyl)propane, 2,2-bis(3,5-dimethyl-4-hydroxyphenyl)propane, 2,2-bis(3,5-dimethyl-4-hydroxyphenyl)propane, bis(2,5-dichloro-4-hydroxyphenyl)propane, and 1,1-bis(4-hydroxyphenyl)phenylethane. The preferred bisphenol (II) is BPA, wherein each $R^1$ is hydrogen, and each $R^2$ is methyl. Deuterated bisphenols for use in the preparation of deuterated indane bisphenols are also commercially available from Aldrich Chemical Company, Inc. or Cambridge Isotope Lab., Inc. or may be conveniently prepared in accordance with conventional preparatory procedures. The remaining reagents and reactants used in the process described below are readily available through commercial sources.

In carrying out the process of the invention, the starting bisphenol of structure (II) is mixed with catalytic amounts of an acidic clay catalyst, namely Montmorillonite K10, which is commercially available from Aldrich. Montmorillonite K10 is prepared by the chemical processing of the mineral montmorillonite $(Al_2O_3 \cdot 4SiO_2 \cdot xH_2O)$ and has a high surface area (220–270 $m^2/g$) Surprisingly, it is discovered that Montmorillonite K10 catalyzes the indane bisphenol synthesis reaction more rapidly and more efficiently than activated clay catalysts previously disclosed in the prior art.

For use in the present process, the amount of Montmorillonite K10 clay catalyst typically varies between about 10–70 g per kilogram of bisphenol. For maximum yield, thirty grams of Montmorillonite K10 per kilogram of bisphenol is preferred. However, higher amounts within the range cause the reaction to proceed more rapidly.

The mixture of bisphenol (II) and clay catalyst is heated at temperatures within the range of about 100°–180° C., preferably about 130°–150° C., during which the bisphenol reactant of structure (II) melts rapidly. The reaction commences, generating a substituted or unsubstituted phenol illustrated by structure (III) above, which dissolves the remaining reactants and products into a solution that is typically dark purple in color. The reaction may be conducted in the melt or in solution in a suitable high boiling organic medium such as toluene, ethylbenzene, cumene, benzene, chlorobenzene, 1,2-dichlorobenzene, and 1,2,4-trichlorobenzene.

The time required for completion of the reaction depends on the reaction temperature, the amount of catalyst used, and whether the reaction is conducted in the melt or in solution. For example, when conducted in the melt at temperatures of at least 150° C., the reaction may be complete in as little as 15 minutes, but when lower temperatures are employed or when the reaction is run in solution, longer reaction times of up to 5 hours or greater may be required depending on the amount of clay present. For example, in reactions run in the melt at 130° C. with 30 g clay per kilogram of BPA, the ideal stopping point, as described below, is reached at about 3.0 hours. When the reaction is run at 130° C. with 60 g clay per kilogram of BPA, the reaction is preferably stopped at about 1.0 hour. The ideal time for stopping the reaction can be cut to 15–35 minutes when the reaction temperature is raised to about 150° C., and the catalyst is present at 30 g per kilogram bisphenol (II). When conducted in solution in an organic medium, the reaction is conducted at reflux for a longer period of time, typically at least 5 hours.

As shown in the depiction of the reaction above, the stoichiometry requires that when two moles of bisphenol (II) react, one mole of indane bisphenol (I) and two moles of phenol (III) are formed. Thus, when BPA is used as the reactant, the final reaction mixture should, theoretically, contain 58.8% by weight IBP and 41.2% by weight phenol by-product. In practice, however, within the above-mentioned ranges of temperature, catalyst, and time, these yields are not fully realized. In the reaction of BPA, the major impurities in the reaction mixture are unreacted BPA and SBI, the decomposition product of IBP. When other bisphenols of structure (II) are used in the reaction, the impurities are unreacted bisphenols (II) and substituted and unsubstituted spirobiindane bisphenols represented as formula (IV)

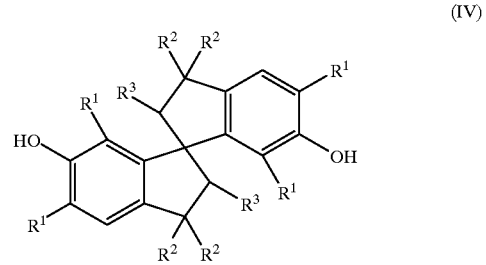

(IV)

wherein $R^1$, $R^2$, and $R^3$ are as defined above. In SBI, each $R^1$ and $R^3$ is hydrogen, and each $R^2$ is a methyl group.

HPLC data adjusted for individual component response factor shows that in the case of BPA, as the reaction progresses, BPA levels drop below 5% by weight; SBI levels rise steadily to 10–15% by weight; phenol by-product levels rise slowly to 45% by weight; and IBP levels rise to 30–38% by weight very rapidly, then show a slow decrease over time as some product is converted to SBI. This formation of SBI also produces phenol, which accounts for the additional phenol present in the reaction mixture.

Throughout the reaction, the amount of bisphenol reactant (II) present steadily declines. While the bisphenol is a challenging impurity to remove, the spirobiindane bisphenol of structure (IV)) is even more persistent in the isolated crystals. Additionally, the presence of the spirobiindane bisphenol in high levels may significantly inhibit precipitation of indane bisphenol from the organic solvent. For these reasons, it is advantageous to stop the reaction before the spirobiindane bisphenol level rises above 10%. The aforementioned preferred combinations of time, temperature, and catalyst amount were developed with this condition in mind. In addition, because of the complications involved in purification when high amounts of spirobiindane bisphenol are produced, it is not recommended that the reaction be carried out with the vacuum distillation of phenol from the reaction mixture.

An important and surprising aspect of the present invention is shown in the case where the reaction is performed in the melt. When the reaction temperature is raised to 150° C. and the catalyst is present at 30 g per kilogram bisphenol (II), the ideal time for stopping the reaction under these conditions can then be dramatically reduced to 15–35 minutes. Also surprisingly, this reduction in reaction time is accompanied with slight increases in the amount of indane bisphenol product formed by the reaction. In addition, as evidenced by mixtures of BPA and clay catalyst, the reaction run at 150° C. produces low percentages of spirobiindane bisphenol impurities (SBI) at 15–35 minutes but contains about 17% unreacted bisphenol (BPA). Continuing the reaction lowers the level of bisphenol (II), but also lowers indane bisphenol (I) product levels, as indane bisphenol is converted to the corresponding spirobiindane bisphenol impurity. Levels of phenol (III) are low after 15–35 minutes at 150° C. but increase rapidly as the reaction proceeds over a longer period of time.

When the reaction is stopped, a suitable organic solvent is added to the crude indane bisphenol product, by-products, and impurities, which are in admixture with the clay catalyst. The amount by weight of organic solvent added is approximately 1–2 times that of the starting bisphenol (II). Suitable organic solvents include toluene, ethylbenzene, cumene, benzene, chlorobenzene, trichloroethane, and tetrachloroethane. To be useful, the organic solvent must be capable of retaining the by-products in solution while allowing the indane bisphenol product to crystallize selectively, as described below. Toluene is the preferred organic solvent.

The reaction products, by-products, and impurities are then dissolved in the organic solvent, typically by heating the mixture to about 100° C. A product solution containing the organic solvent and the dissolved crude indane bisphenol, by-products, and impurities is then formed in admixture with the clay. The Montmorillonite K10 clay catalyst is removed, typically by filtering the product solution and the undissolved catalyst through a slurry of CELITE® filter agent. A transparent brown filtrate is generally produced, and the dark purple contaminants are removed during the filtration.

Alternatively, the organic solvent can be added to the mixture of bisphenol (II) and clay catalyst before the reaction begins. As mentioned above, 1–2 g of organic solvent is added for every 1 g of bisphenol (II) reactant. In this case, it is necessary to heat the reaction mixture at reflux, preferably for at least 5 hours, to allow the reaction to proceed to the ideal stopping point mentioned above. After the reaction is stopped, the entire product solution containing the clay catalyst is filtered, typically through CELITE®, as described above.

Crude crystals containing the indane bisphenol product precipitate as the filtered product solution is allowed to cool slowly to a temperature ranging between about 0° C. and room temperature, typically for a time of about 8–24 hours. Quantitative analysis by HPLC indicates that about 65% of the indane bisphenol (I) produced by the present reaction crystallizes in these crystals. These crude crystals, which are roughly 70% pure by weight, can then be recovered by conventional methods such as vacuum filtration and can then be washed with organic solvent. As described below, the reaction yield can be increased by recovering additional crude crystals which are contained in the product solution remaining after this precipitation step.

Surprisingly, further purification of the crude indane bisphenol product is effected by dissolution in acetic acid followed by a second precipitation. This is unexpected because, as taught by the Japanese patent application referenced above, polar solvents are generally undesirable for the recrystallization and purification of indane bisphenols. Also surprising, precipitation from acetic acid results in indane bisphenol crystals having a higher purity ($\geq 97\%$) than was previously possible using aromatic solvents.

The recrystallization may be from an acetic acid solution that is about 20% solids (crude crystals) by weight dissolved in aqueous acetic acid preferably ranging in concentration from about 45%–80% by volume acetic acid. Alternatively, and preferably, before the second precipitation, the crude crystals are dissolved in a volume of pure acetic acid that is then diluted with water to the aforementioned concentrations. As used herein, "pure acetic acid" refers to reagent grade acetic acid that is typically greater than 99.7% pure. However, before dilution with water, it is preferable to mix activated carbon as a decolorizing agent with the pure acetic acid containing the dissolved crude indane bisphenol crystals, followed by filtration. The acetic acid filtrate is then diluted with the amount of deionized water necessary to achieve the above concentration.

As stated above, after the second precipitation from the acetic acid solution, a high purity indane bisphenol, defined herein as being at least 97% pure, but may be up to about 99% pure, is formed. This typically represents about 23–30% of the theoretical yield for the reaction. The high purity indane bisphenol crystals produced by the present method are also referred to herein as "second crop" crystals.

The high purity indane bisphenol which is produced can then be isolated in sufficient purity for use as a starting material for low molecular weight indane polymers. However, for many purposes, including the preparation of high molecular weight homo- and copolymers containing indane bisphenol moieties, further purification may be necessary.

Surprisingly, the purity of the high purity indane bisphenol crystals is improved and can be maximized by performing at least one recrystallization (defined herein as dissolution followed by precipitation) from an aqueous acetic acid solution which ranges in concentration from about 45% to 80% by volume acetic acid. Typically, the aqueous acetic acid solution contains from about 20% to about 50% solids by weight. Alternatively, the second crop crystal can be further purified by recrystallization from a solution which is about 89–93% by volume toluene and about 7–11% by volume n-propanol and which typically contains 20% to 30% solids by weight. If necessary, generally in cases where the purity of the second crop crystal is less than 98%, intermediate crystals formed after precipitation from the n-propanol/toluene solution described above may be further purified by recrystallization from an aqueous acetic acid solution, as characterized above. Alternatively, second crop crystals may be first recrystallized from the above aqueous acetic acid solution to produce intermediate crystals which can be further purified from a n-propanol/toluene solution, as specified above. Each of these techniques of further purification leads to a high purity indane bisphenol in substantially pure form, with little loss in overall yield. As used herein, the term "in substantially pure form" means a high purity indane bisphenol having a purity of greater than 99%.

Another advantage of the present invention is that it provides a method of increasing product yield through the recovery of additional indane bisphenol product which remains in the product solution after the aforementioned precipitation of crude crystals from the product solution. In addition to unprecipitated indane bisphenol, the product solution remaining after the crude crystal precipitation, contains the major proportion of by-products and impurities including phenols of formula (III), spirobiindane bisphenols as represented by formula (IV), and unreacted bisphenol of formula (II).

To recover additional crude crystals of indane bisphenol, the remaining product solution is removed from the precipitated crude crystals, typically by filtration. Next, the solvents (organic solvent and phenol by-product) are removed or stripped from the filtrate solution. A conventional rotary evaporator may be used. The remaining material, which includes additional crude indane bisphenol, spirobiindane bisphenol of formula (IV), and unreacted bisphenol of formula (II), can then be dissolved in an organic liquid, such as one of the organic solvents previously mentioned or 45%–80% by volume aqueous acetic acid, to form a solution that is typically about 50% solute by weight. Crude crystals containing additional crude indane bisphenol precipitate from the solution, typically after allowing the solution to sit for approximately 24–48 hours. Conventional vacuum filtration can then be used to recover the crude crystals. These crude crystals can be further purified by selective recrystallization from aqueous acetic acid, as mentioned above, to produce additional high purity indane bisphenol (second crop crystals). In the case of IBP, the additional product gained in this step pushes the overall yield of the high purity indane bisphenol to 51% of the IBP actually produced and 34% of the theoretical yield.

The method of this invention is illustrated in the following examples. Use of BPA for the production of IBP in the examples is for illustrative purposes only, and one of ordinary skill in the art would understand that the invention is not limited to the use of BPA, and that other substituted bisphenols may be used instead to produce corresponding indane bisphenols of formula (I).

Quantitative analyses of product samples were performed by HPLC. Melting point analyses of IBP samples to verify product purity were performed at a heating rate of 10° C./min. using a differential scanning calorimeter (DSC). IBP produced and purified according to the present method consistently exhibited very low UV absorption at 350 nm, especially in comparison with commercially prepared pure BPA from which it was derived.

Preparation of High Purity Indane Bisphenol

EXAMPLE 1

(i) 1.5 kg BPA (6.57 mol) were placed in a 5 L three-neck round bottomed flask with 45 g of Montmorillonite K10 clay. The system was equipped with a mechanical stirrer and a nitrogen atmosphere. The mixture was heated at 130° C. for 5 hours past the point at which the contents of the flask became a dark purple liquid. Samples of the reaction mixture taken throughout the 5 hour time period indicated that the formation of IBP reached a plateau at 1.5–2 hours. At this point, the mixture contained 15–17% BPA and 8% SBI, as indicated by HPLC. After 4.5 to 5 hours BPA levels fell below 10%. Quantitative analysis of the reaction mixture revealed that after 5 hours, the reaction mixture contained 31% IBP by weight (479 g, 1.78 mol), which is about 54% of the theoretical yield. Toluene (1.5 L) was added to the reaction mixture by addition funnel, and the solution was heated with stirring to 100° C. The clay catalyst was then filtered off through a slurry of CELITE® filter agent, and the light brown filtrate was allowed to cool overnight to precipitate 450 g of crude crystal. Quantitative analysis showed that of this mass, 63% was IBP (70% pure), representing a recovery of 62% of the IBP produced in the reaction.

(ii) The crystals from step (i) were washed with 500 mL of toluene and placed in a 2 L Erlenmeyer flask to which was added 2 mL pure acetic acid for each gram of crude crystal recovered. The flask was heated while stirring until the crystals dissolved, and activated carbon was added as a decolorizing agent. The suspension was filtered through fluted filter paper into a 4 L Erlenmeyer flask. While heating and stirring the light brown filtrate, a volume of deionized water equal to the amount of acetic acid used to dissolve the crystal was added. The result was a 50% aqueous solution of acetic acid containing 20% solids by weight. Heating and stirring continued until all of the solid dissolved. The heat was removed, and the solution cooled overnight. A white crystalline solid precipitated from the solution which was then collected by vacuum filtration and rinsed with 300 mL of a 50% aqueous solution of acetic acid. The resulting high purity IBP crystals (second crop crystals) were 98% pure, as indicated by HPLC, and had a mass of 237.11 g. This represents an 83% recovery for the acetic acid recrystallization, a recovery of 47% of the IBP actually produced in the reaction and 27% of the overall theoretical yield for the reaction.

EXAMPLE 2

The procedure of Example 1 was repeated except that in step (i), the reaction was run at 150° C. for 20 minutes past the point at which the contents of the flask became a dark purple liquid. Analysis by HPLC of samples taken after the 20 minute period indicated that the mixture contained 38% IBP by weight or about 67% of the theoretical yield, a higher amount than produced by the lower temperature reaction of Example 1. The mixture also contained 17% BPA, 9% SBI, and 29% phenol by weight. After addition of toluene, heating, removal of the clay catalyst, and cooling, 496 g of crude crystal precipitated.

The purification procedure of step (ii) of Example 1 was then followed. The resulting high purity IBP (second crop crystals) were 97.4% pure, as indicated by HPLC, and had a mass of 260 g (30% of the theoretical yield). A sample of these crystals exhibited a melting point of 197.1° C., as analyzed by DSC.

EXAMPLE 3

The procedure of Example 1 was followed except that 90 g of Montmorillonite K10 clay were used in the reaction, and the reaction was conducted for 1.5 hours past the point the contents of the flask became a dark purple liquid. After 1.5 hours, the reaction mixture contained 32% IBP by weight. BPA and SBI levels were both relatively low at 11.4% and 9.6%, respectively. The IBP second crop crystals were 97.5% pure, as indicated by HPLC, and had a mass of 233 g. This represents a recovery of 48% of the IBP actually produced in the reaction and 26% of the overall theoretical yield for the reaction.

EXAMPLE 4

150 g of BPA (0.657 mol) were placed in a 1 L three-neck round bottom flask with 4.5 g Montmorillonite K10 clay and 150 mL toluene. The mixture was heated at reflux for 5 hours. The reaction mixture was then filtered and worked up using the procedure described in steps (i) and (ii) of Example 1. The high purity IBP second crop crystals were 97.98% pure by HPLC and had a mass of 26 g. This represents a recovery of 30% of the overall theoretical yield for the reaction.

Preparation of High Purity Indane Bisphenol in Substantially Pure Form

EXAMPLE 5

10 g of the second crop crystal of IBP from Example 1 (98% pure) were partially dissolved in 50 mL of 80% aqueous acetic acid. The solution was heated to reflux with a moderate stir rate. When all of the IBP had gone into solution, the beaker was removed from the heat, covered, and set on the counter to cool to room temperature allowing IBP to precipitate. The next day these crystals were collected and dried by vacuum filtration and dried overnight in an oven under vacuum to remove any remaining solvent. IBP crystals (8.20 g) were recovered having a purity of >99%, as indicated by HPLC, a melting point of 197.9° C., as shown by a clean, sharp peak by DSC analysis, and an absorption of <0.001 at 350 nm (1 g/100 mL MeOH).

EXAMPLE 6

10 g of second crop crystal of IBP from Example 1 (98% pure) were partially dissolved in 2.6 mL n-propanol and 30 mL toluene. The solution was heated to reflux with a moderate stir rate. When all of the IBP had gone into solution, the beaker was removed from the heat, covered, and set on the counter to cool to room temperature allowing IBP to precipitate. The next day these crystals were collected, dried by vacuum filtration, then dried overnight in an oven under vacuum to remove any remaining solvent. IBP crystals (8.07 g) were recovered having a purity of >99%, as indicated by HPLC, a melting point of 197.1° C., as shown by a clean, sharp peak by DSC analysis, and an absorption of <0.001 at 350 nm (1 g/100 mL MeOH).

EXAMPLE 7

100 g of the second crop crystal of IBP from Example 2 (97.4% pure) were partially dissolved in 500 mL of 75% by volume aqueous acetic acid. The solution was heated to reflux until all of the IBP had gone into solution. The beaker was removed from the heat, covered, and set on the counter to cool to room temperature allowing the crystals to precipitate. The next day these crystals were collected, dried by vacuum filtration, then dried overnight in an oven under vacuum to remove any remaining solvent. Intermediate IBP crystals (84.9 g) were recovered.

Of the intermediate crystals, 51.0 g were partially dissolved in 128 mL of 75% by volume aqueous acetic acid. The solution was heated to reflux until all of the IBP had gone into solution. After cooling to room temperature, IBP precipitated, and the precipitate was dried thoroughly in the vacuum oven. The recovered IBP crystals (46.6 g) were >99% pure, as indicated by HPLC, exhibited a melting point of 197.0° C., as shown by a clean, sharp peak by DSC analysis, and showed an absorption of 0.001 at 350 nm (1 g/100 mL MeOH).

The remaining 33.9 g of intermediate IBP crystals from the 75% aqueous acetic acid recrystallization above were dissolved partially in 15 mL of n-propanol and set over medium heat with a moderate stir rate. Toluene (173 mL), heated to just below the reflux temperature, was then added slowly to the IBP solution, and the mixture was heated to reflux for approximately 45 seconds. The solution was removed from heat, covered, and set aside to cool to precipitate IBP. The recovered crystals (28.1 g) were >99% pure, as indicated by HPLC, exhibited a melting point of 195.3° C. shown by a sharp, clean peak, and showed an absorption of 0.003 at 350 nm (1 g/100 mL MeOH).

Additional Yield

EXAMPLE 8

3000 mL of filtrate obtained in Example 1 after the first precipitation step (i) from toluene were placed on a rotary evaporator to distill and remove toluene and phenol. When 600 mL of solid dissolved in phenol remained, the solution was dissolved in 600 mL of toluene and allowed to precipitate overnight. The crude crystal was collected and recrystallized from 50% by volume aqueous acetic acid, according to the procedure described in step (ii) of Example 1. The process yielded an additional 40 g of IBP comparable in purity to the second crop crystal from Example 1 (98%), as indicated by HPLC and DSC. This step increased the overall yield of second crop crystal to 51% IBP actually produced and 34% of the theoretical yield.

While the invention has been particularly shown and described with reference to the preferred embodiments thereof, it will be understood by those skilled in the art that other changes in form and details may be made therein without departing from the spirit and scope of the invention.

We claim:

1. A method for preparing a high purity indane bisphenol of the formula

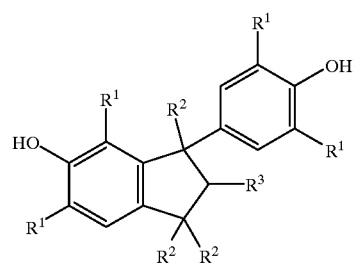

(I)

wherein each $R^1$ is independently hydrogen, deuterium, halogen, alkyl having 1 to 4 carbons, alkoxy having 1 to 4 carbons, or a deuterated equivalent thereof; each $R^2$ is an alkyl group having 1 to 4 carbons or a deuterated equivalent thereof;

$R^3$ is hydrogen or deuterium when $R^2$ is methyl or its deuterated equivalent;

otherwise $R^3$ is an alkyl group or a deuterated equivalent thereof having one less carbon than that of $R^2$;

wherein said method comprises the steps of
(a) heating a mixture comprising
(i) a bisphenol having the formula

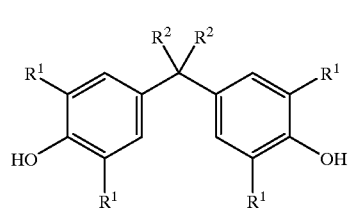

(II)

wherein $R^1$ and $R^2$ are as previously defined; and
(ii) a clay catalyst comprising Montmorillonite K10 at a temperature in the range of about 100°–180° C. for a time sufficient to produce a crude indane bisphenol, by-products, and impurities in admixture with said clay catalyst;
(b) adding an organic solvent to said crude indane bisphenol, by-products, impurities, and said clay catalyst, wherein said organic solvent is selected from the group of toluene, ethylbenzene, cumene, benzene, chlorobenzene, trichloroethane, and tetrachloroethane;

(c) dissolving in said organic solvent said crude indane bisphenol, by-products, and impurities to form a product solution in admixture with said clay catalyst;

(d) removing said clay catalyst from said product solution;

(e) allowing crude crystals containing said crude indane bisphenol to precipitate from said product solution;

(f) recovering said crude crystals; and (g) further purifying said crude crystals by dissolution in acetic acid followed by a second precipitation.

2. The method of claim 1, wherein said heating step (a) is conducted in the melt.

3. The method according to claim 2, wherein said temperature of said heating step (a) is about 130° C. and wherein said heating step (a) continues for a time within the range of about 1 to about 3 hours.

4. The method according to claim 2, wherein said temperature of said heating step (a) is about 150° C. and wherein said heating step (a) continues for a time within the range of about 15 to about 35 minutes.

5. The method of claim 1, wherein said heating step (a) is conducted in solution at reflux and continues for a time of at least 5 hours.

6. A method for preparing a high purity indane bisphenol of the formula

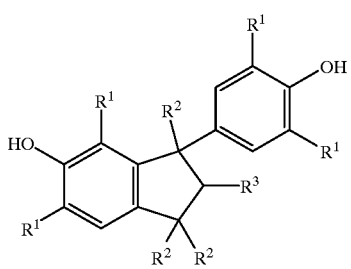

(I)

wherein each $R^1$ is independently hydrogen, deuterium, halogen, alkyl having 1 to 4 carbons, alkoxy having 1 to 4 carbons, or a deuterated equivalent thereof; each $R^2$ is an alkyl group having 1 to 4 carbons or a deuterated equivalent thereof;

$R^3$ is hydrogen or deuterium when $R^2$ is methyl or its deuterated equivalent;

otherwise $R^3$ is an alkyl group or a deuterated equivalent thereof having one less carbon than that of $R^2$;

wherein said method comprises the steps of (a) heating a mixture at reflux, wherein said mixture comprises (i) a bisphenol having the formula

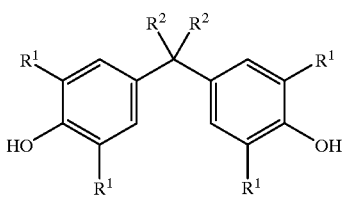

(II)

wherein $R^1$ and $R^2$ are as previously defined;

(ii) a clay catalyst comprising Montmorillonite K10; and (iii) an organic solvent selected from the group of toluene, ethylbenzene, cumene, benzene, chlorobenzene, trichloroethane, and tetrachloroethane at a temperature in the range of about 100°–180° C. for a time sufficient to produce a product solution in admixture with said clay catalyst, wherein said product solution comprises said organic solvent, a crude indane bisphenol, by-products, and impurities;

(b) removing said clay catalyst from said product solution;

(c) allowing crude crystals containing said crude indane bisphenol to precipitate from said product solution;

(d) recovering said crude crystals; and (e) further purifying said crude crystals by dissolution in acetic acid followed by a second precipitation.

7. The method according to claim 6, wherein said heating step (a) continues for a time of at least 5 hours.

8. The method according to claim 1 or 6, wherein in step (a), the amount of said Montmorillonite K10 clay in said mixture is between about 10 g and 70 g per kilogram of said bisphenol of formula (II).

9. The method according to claim 1 or 6, wherein each $R^1$ is hydrogen, $R^2$ is methyl, and $R^3$ is hydrogen.

10. The method according to claim 1 or 6, wherein said recovering step comprises:

removing from said crude crystals said product solution remaining after said crude crystals have precipitated, wherein said remaining product solution contains a major proportion of said by-products and said impurities including phenols of the formula

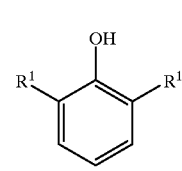

(III)

spirobiindane bisphenols of the formula

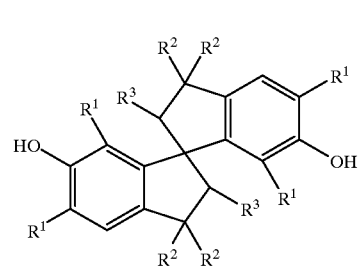

(IV)

and unreacted bisphenol of formula (II), wherein $R^1$, $R^2$, and $R^3$ are as previously defined.

11. The method according to claim 10 further comprising the steps of:

removing said organic solvent and said phenols of formula (III) from said remaining product solution to leave a material comprising an additional crude indane bisphenol, said spirobiindane bisphenol of formula (IV), and said unreacted bisphenol of formula (II);

dissolving said material in an organic liquid followed by an additional precipitation of crude crystals containing said additional crude indane bisphenol; and removing said crude crystals from said organic liquid.

12. The method according to claim 11, wherein said organic liquid is selected from the group of toluene, xylene, ethylbenzene, cumene, benzene, chlorobenzene, trichloroethane, tetrachloroethane, and 45%–80% by volume aqueous acetic acid.

13. The method according to claim 1 or 6, wherein said acetic acid is aqueous acetic acid ranging in concentration from about 45%–80% by volume acetic acid.

14. The method according to claim 1 or 6, wherein said acetic acid is pure acetic acid, and wherein prior to said second precipitation, said method further comprises the step of diluting with water said pure acetic acid and said dissolved crude crystals to form an aqueous acetic acid solution ranging in concentration from about 45%–80% by volume acetic acid.

15. The method according to claim 1 or 6, wherein said acetic acid is pure acetic acid, and wherein prior to said second precipitation, said method further comprises the steps of:

mixing activated carbon with said pure acetic acid and said dissolved crude crystals, followed by filtration; and diluting the filtrate with water to provide an aqueous acetic acid solution containing said dissolved crude crystals, wherein said acetic acid is present in an amount ranging from about 45%–80% by volume.

16. The method according to claim 1 or 6 further comprising the step of:

further purifying said high purity indane bisphenol by at least one recrystallization, wherein the first recrystallization comprises dissolving said high purity indane bisphenol in an aqueous acetic acid solution ranging in concentration from about 45%–80% by volume acetic acid, followed by precipitation, and wherein any subsequent recrystallization comprises dissolving the precipitate from the immediately prior recrystallization in an aqueous acetic acid solution containing from about 45% to 80% by volume acetic acid, followed by precipitation, thereby producing said high purity indane bisphenol of formula (I) in substantially pure form.

17. The method according to claim 1 or 6 further comprising the step of:

further purifying said high purity indane bisphenol by dissolution in a solution which contains from about 89–93% by volume toluene and from about 7–11% by volume n-propanol, followed by precipitation to produce said high purity indane bisphenol of formula (I) in substantially pure form.

18. The method according to claim 1 or 6 further comprising the steps of:

further purifying said high purity indane bisphenol by dissolution in a solution which contains from about 89–93% by volume toluene and from about 7–11% by volume n-propanol, followed by precipitation to form intermediate crystals; and dissolving said intermediate crystals in an aqueous acetic acid solution which contains from about 45% to 80% by volume acetic acid, followed by precipitation, to produce said high purity indane bisphenol of formula (I) in substantially pure form.

19. The method according to claim 1 or 6 further comprising the steps of:

further purifying said high purity indane bisphenol by dissolution in an aqueous acetic acid solution which contains from about 45% to 80% by volume acetic acid, followed by precipitation to form intermediate crystals; and dissolving said intermediate crystals in a solution which contains from about 89–93% by volume toluene and from about 7–11% by volume n-propanol, followed by precipitation to produce said high purity indane bisphenol of formula (I) in substantially pure form.

* * * * *